United States Patent

Ebihara et al.

[11] Patent Number: 6,118,007
[45] Date of Patent: Sep. 12, 2000

[54] PREPARATION PROCESS OF NITROGUANIDINE DERIVATIVES

[75] Inventors: Koichi Ebihara; Tatsuo Kaiho; Michihiko Miyamoto; Daisuke Ura, all of Fukuoka, Japan

[73] Assignee: Mitsui Chemicals, Inc., Japan

[21] Appl. No.: 09/046,588

[22] Filed: Mar. 24, 1998

[30] Foreign Application Priority Data

| | | | |
|---|---|---|---|
| Mar. 31, 1997 | [JP] | Japan | 9-080178 |
| Apr. 1, 1997 | [JP] | Japan | 9-082838 |
| Aug. 20, 1997 | [JP] | Japan | 9-223813 |
| Sep. 24, 1997 | [JP] | Japan | 9-258968 |
| Dec. 17, 1997 | [JP] | Japan | 9-347934 |

[51] Int. Cl.[7] ............ C07D 277/28; C07D 263/30; C07D 333/22
[52] U.S. Cl. ............ 548/205; 564/237; 564/240; 546/332; 548/235; 549/74
[58] Field of Search ............ 564/237, 240; 546/332; 548/205, 235; 549/74

[56] References Cited

FOREIGN PATENT DOCUMENTS

| | | |
|---|---|---|
| 0428941 | 5/1991 | European Pat. Off. |
| 0483055 | 4/1992 | European Pat. Off. |
| 0483062 | 4/1992 | European Pat. Off. |
| 2-288860 | 11/1990 | Japan |
| 3-109374 | 5/1991 | Japan |
| 3-157308 | 7/1991 | Japan |
| 3-291267 | 12/1991 | Japan |
| 4-74158 | 3/1992 | Japan |
| 4-120054 | 4/1992 | Japan |
| 4-330049 | 11/1992 | Japan |
| 5-9173 | 1/1993 | Japan |
| 7-179448 | 7/1995 | Japan |
| 10-7645 | 1/1998 | Japan |

OTHER PUBLICATIONS

Knapp et al, "Amino Protection Using Triazones", *Tetrahedron Letters*, vol. 31, No. 15, 1990, pp. 2109–2112, XP002067348.

Chemical Abstracts, vol. 123, No. 19, Nov. 6, 1995, Columbus, Ohio, U.S., Abstract No. 256770p, Odaka et al, "Preparation of 1–(tetrahydro–3–furanylmethyl)–2–(nitroimino)–1,3,5–triazine Derivatives as Insecticides and Method for Production Thereof", p. 1164, col. 1, XP002067349 *abstract* & JP07173157A (Mitsui Toatsu Chemicals, Inc.) Jul. 11, 1995.

*Primary Examiner*—Peter O'Sullivan
*Attorney, Agent, or Firm*—Burns, Doane, Swecker & Mathis, L.L.P.

[57] ABSTRACT

A process, as a substitute for hydrolysis, for preparing a nitroguanidine derivative represented by the following formula (2):

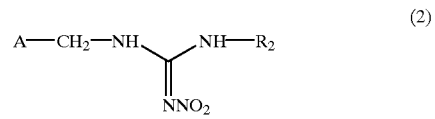

(2)

wherein A represents a substituted or unsubstituted aromatic or non-aromatic hydrocarbon ring, a substituted or unsubstituted aromatic or non-aromatic heterocycle, a hydrogen atom or a substituted or unsubstituted alkyl, alkenyl or alkynyl group; and $R_2$ represents a hydrogen atom, a substituted or unsubstituted $C_{1-6}$ alkyl, alkenyl or alkynyl group, which comprises reacting a compound represented by the following formula (1):

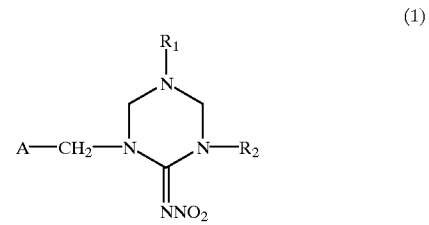

(1)

wherein $R_1$ represents a substituted or unsubstituted, linear or cyclic $C_{1-10}$ alkyl group and A and $R_2$ have the same meanings as defined above, with ammonia, a primary amine or a secondary amine, or a salt thereof.

7 Claims, No Drawings

PREPARATION PROCESS OF NITROGUANIDINE DERIVATIVES

BACKGROUND OF THE INVENTION

1. Field of the Invention

This invention relates a novel preparation process of nitroguanidine derivatives.

The process of the present invention is very useful upon preparation of a compound employed as an agricultural chemical (particularly, an insecticide) or an intermediate therefor.

2. Description of the Related Art

It is well known that certain nitroguanidine derivatives are useful as an agricultural chemical (particularly an insecticide) or intermediate therefor (Japanese Patent Laid-Open Nos. 288860/1990, 109374/1991, 157308/1991, 179448/1995).

Preparation processes of a di-substituted nitroguanidine as follows are known.

(1) A process of hydrolyzing a 1,3,5-tri-substituted 2-nitroiminohexahydro-1,3,5-triazine in the presence of an acid (Japanese Patent Laid-Open Nos. 291267/1991, 330049/1992).

Reaction Formula (1)

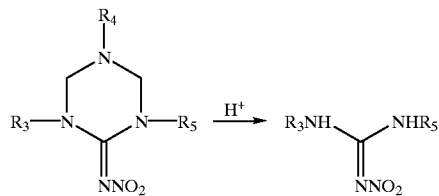

(2) A process of preparing via a certain isothiourea (Japanese Patent Laid-Open No. 9173/1993)

Reaction Formula (2)

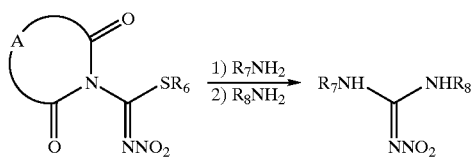

(3) A process of preparing via a certain dithiocarbamic acid derivative (Japanese Patent Laid-Open Nos. 120054/1992, 74158/1992).

Reaction Formula (3)

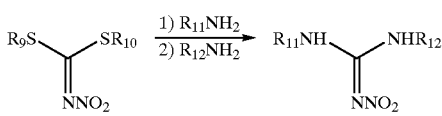

(4) A process of preparing via a 1,2-di-substituted-3-nitroisothiourea (Japanese Patent Laid-Open No. 288860/1990).

Reaction Formula (4)

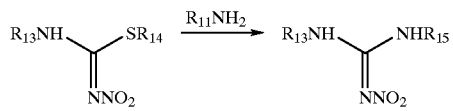

(5) A process of alkylating a mono-substituted nitroguanidine directly (Japanese Patent Application No. 15814/1996).

Reaction Formula (5)

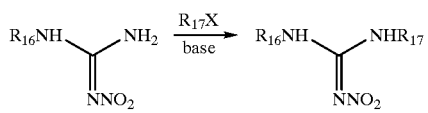

As described above, only the above process (1) is known as a process for preparing a di-substituted nitroguanidine by using 1,3,5-tri-substituted-2-nitroiminohexahydrotriazine as a raw material, but it is a process based on a hydrolytic reaction with an acid.

A nitroguanidine derivative is well known to have a high water solubility. In addition, a nitroguanidine tends to have higher water solubility under acid conditions than under neutral conditions. When the reaction is effected in the presence of water or an acid, a reduction in a crystallization yield or a reduction in an extraction ratio therefore occurs upon the isolating operation, which tends to make the operation troublesome.

If neutralization is conducted in order to suppress such a reduction, a triazine derivative is produced by the reverse reaction, which makes the operation more trouble-some.

SUMMARY OF THE INVENTION

An object of the present invention is therefore to provide a convenient preparation process which can replace hydrolysis.

With a view toward attaining the above object, the present inventors have conducted an extensive investigation on the decomposition process, other than hydrolysis, of 1,3,5-tri-substituted-2-nitroiminohexahydrotriazine. As a result, they have found a process which is different from acid hydrolysis in its decomposition mechanism and comprises reacting it with ammonia, a primary amine or a secondary amine, or a salt thereof by using neither an acid nor water, leading to the completion of the present invention.

In an aspect of the present invention, there is thus provided a process for preparing a nitroguanidine derivative represented by the following formula (2):

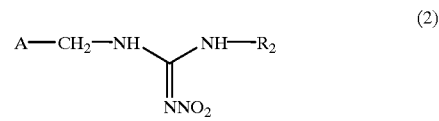

wherein A represents a substituted or unsubstituted aromatic or non-aromatic hydrocarbon ring, a substituted or unsubstituted aromatic or non-aromatic heterocycle, a hydrogen atom or a substituted or unsubstituted alkyl, alkenyl or alkynyl group and $R_2$ represents a hydrogen atom, a substituted or unsubstituted $C_{1-6}$ alkyl, alkenyl or alkynyl group, which comprises reacting a compound represented by the following formula (1):

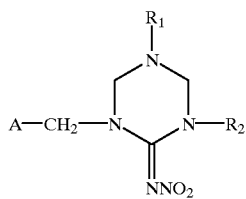

(1)

wherein $R_1$ represents a substituted or unsubstituted linear or cyclic $C_{1-10}$ alkyl group and A and R2 have the same meanings as defined above with ammonia, a primary amine or secondary amine, or a salt thereof.

DETAILED DESCRIPTION OF THE PREFERRED EMBODIMENTS

Typical examples of the substituent A of the compound of the formula (1) usable in the present invention include a hydrogen atom and methyl, ethyl, propyl, isopropyl, butyl, t-butyl, pentyl, hexyl, vinyl, allyl, propargyl, benzyl, methoxymethyl, methylthiomethyl, trifluoromethyl, phenyl, 3-nitrophenyl, 3-cyanophenyl, 3-chlorophenyl, 3-trifluoromethylphenyl, cyclopentyl, cyclohexyl, 2-pyridyl, 3-pyridyl, 2-chloro-5-pyridyl, 2-methyl-5-pyridyl, 2-methoxy-5-pyridyl, 5-thiazolyl, 2-chloro-5-thiazolyl, 2-methyl-5-thiazolyl, 2-chloro-5-pyrimidyl, 2-chloro-5-oxazolyl, 2-methyl-5-oxazolyl, 2-furyl, 3-furyl, 2-tetrahydrofuryl, 3-tetrahydrofuryl, 2-methyl-4-tetrahydrofuryl, 2-ethyl-4-tetrahydrofuryl, 2-iosopropyltetrahydrofuryl, 2-t-butyl-4-tetrahydrofuryl and 2,2-dimethyl-4-tetrahydrofuryl groups. Typical examples of $R_1$ include methyl, ethyl, n-propyl, isopropyl, n-butyl, sec-butyl, isobutyl, t-butyl, pentyl, hexyl, heptyl, octyl, nonyl, decyl, cyclopentyl, cyclohexyl and benzyl groups. Typical examples of $R_2$ include a hydrogen atom and methyl, ethyl, n-propyl, isopropyl, n-butyl, sec-butyl, isobutyl, t-butyl, pentyl, hexyl, cyclopentyl, cyclohexyl, allyl, propargyl, methoxymethyl and methylthiomethyl groups.

Typical examples of the primary or secondary amine usable in the present invention include methylamine, ethylamine, n-propylamine, isopropylamine, n-butylamine, isobutylamine, sec-butylamine, t-butylamine, pentylamine, hexylamine, heptylamine, octylamine, cyclohexylamine, benzylamine, allylamine, propargylamine, aniline, phenylenediamine, toluidine, xylidine, ethylenediamine, trimethylenediamine, dimethylamine, diethylamine, benzylmethylamine, N-methylethylenediamine, N,N'-dimethylethylenediamine, N-methylaniline, pyrrolidine, piperidine, piperazine, N-methylpiperazine, morpholine, thiomorpholine, ethanolamine, diethanolamine, methoxyethylamine, amino acid esters such as methyl aminoacetate, hydrazine, N-methylhydrazine, N,N-dimethylhydrazine, N,N'-dimethylhydrazine, hydroxylamine, methoxyamine and benzyloxyamine.

Among the compounds which react with the compound represented by formula (1), preferred are ammonia and aliphatic amines, with aliphatic cyclic amines being particularly preferred.

As the primary or secondary amine, agents which have a primary or secondary amino group modified on a carrier insoluble in a solvent may be employed. Typical examples of them are given below.

Examples of the carrier include polymer compounds and glass beads. Specific examples of a monomer which forms the polymer compound carrier include aromatic vinyl compounds such as styrene, divinylbenzene and vinylpyridine, acrylates such as acrylic acid ester, methacrylic acid ester, acrylonitrile and acrylamide, phenol compounds such as phenol, cyclic compounds such as ethylene oxide and ethyleneimine and vinyl alcohols. Polymer compounds obtained by polymerizing one or more of these monomers can be used as a polymer compound carrier. Specific examples include polystyrene resins, acrylate resins, methacrylate resins, phenol resins and divinylbenzene-styrene copolymer resins.

Specific examples of the primary or secondary amino group which modifies such a polymer compound carrier or glass beads include amino, methylamino, ethylamino, propylamino, benzylamino, 2-aminoethylamino, 3-aminopropylamino, piperidino and hydrazino groups. A proper spacer may be introduced between such a functional group and a carrier.

Specific examples of the agents obtained by modifying a carrier, which is insoluble in a solvent, with a primary or secondary amine include amino-containing anionic exchange resins such as "Lewatit OC1059, OC1065, R258-K and E82/81" (trade names; each, product of Bayer AG), "Diaion WA20, WA21 and CR20, Sepabeads FP-HA13, FP-BA13 and FP-ZA13" (trade names; each, product of Mitsubishi Chemical Co., Ltd.), "Amberlite IRA6E" (trade name; product of Rohm & Haas Co.), "Aminopropyl-CPG" (trade name; product of CPG Inc.) and "Aminocellulofine" (trade name; product of Chisso Corporation).

Ammonia or amine can also be used in the form of a salt. Specific examples of an acid which forms a salt with such an amine include mineral acids such as hydrochloric acid, sulfuric acid, phosphoric acid and carbonic acid; organic carboxylic acids such as formic acid and acetic acid and organic sulfonic acids such as methanesulfonic acid and toluenesulfonic acid. These salts may be used either in the form of an anhydride or hydrate.

It is recommendable that ammonia or amine to be used in the present invention contains at least one equivalent of a primary or secondary amino group based on the compound represented by the formula (1), with at least 2 equivalents being preferred. The amine in the form of a salt, on the other hand, may contain it in an amount of at least 0.01 equivalent based on the compound represented by the formula (1), with at least 0.1 equivalent being preferred.

The reaction can be carried out in a solventless manner but is generally conducted by diluting with a solvent. Examples of the solvent include ethers such as tetrahydrofuran and dioxane, halogenated hydrocarbons such as dichloromethane and dichloroethane, ketones such as acetone and methyl ethyl ketone; nitrites such as acetonitrile, aprotic polar solvents such as N,N-dimethylformamide, 1,3-dimethyl-2-imidazolidinone, dimethylsulfoxide and N-methylpyrrolidone, and alcohols such as methanol, ethanol, propanol, isopropanol, butanol, isobutanol and ethylene glycol. Among them, preferred are halogenated hydrocarbons such as dichloromethane or alcohols, with alcohols being particularly preferred. They can be used as a solvent mixture after mixed in an optional ratio. Alternatively, they can be used as a mixture with water.

The reaction temperature may preferably be 10° C. or higher, with 30 to 120° C. being particularly preferred.

The reaction time may generally be 0.1 hour to 7 days, with 1 to 24 hours being preferred.

The reaction can be effected either at normal pressure or under pressure.

After the reaction, it is possible to carry out treatment in a manner known per se in the art. For example, the target product can be obtained by removing salts from the reaction mixture through filtration or the like as needed and then, cooling the residue or adding thereto a poor solvent to cause crystallization. Alternatively, the target product can be obtained by filtering the reaction mixture to remove therefrom salts as needed and then concentrating the residue. The product of a higher purity is available by washing with water, treatment with activated charcoal, recrystallization or the like as needed.

The nitroimino-containing compound represented by the formula (1) or (2) may exist as isomers (syn- and anti-isomers) and tautomers. When A represents a tetrahydrofuran ring or the like in the formulas (1) and (2), an asymmetric carbon exists so that the compound represented by the formula (1) or (2) may exist as an optically active isomer or racemic modification, or a mixture containing them at an optional ratio. Any of such isomers and tautomers, and mixtures thereof are embraced in the scope of the present invention.

The following advantages can be obtained by the process of the present invention.

(1) A preparation process based on hydrolysis is accompanied with the drawbacks that owing to the existence of water or an acid in the reaction system, crystallization or purification cannot be carried out easily, and inorganic salts formed by neutralization are inevitably mixed in the system, which requires an additional cumbersome operation such as silica gel purification. The process of the present invention, on the other hand, does not need such a troublesome operation.

(2) A solubility of a nitroguanidine derivative in an aqueous phase increases under high acid conditions upon neutralization with an acid, which lowers an extraction ratio or crystallization yield. When the reaction mixture becomes nearly alkaline or neutral by neutralization, a triazine derivative which is a raw material is reproduced, which causes a reduction in a yield or purity. It is therefore necessary to carry out severe pH control upon neutralization. Thus, the conventional process based on hydrolysis is markedly troublesome. The process of the present invention makes it possible to omit the pH control.

The advantages as described in (1) can be confirmed by comparison between Comparative Example 1 and Example 1, and between Comparative Example 2 and Example 3. Those in (2) can be confirmed by comparison between Comparative Example 3 and Example 10, and so on.

According to the process of the present invention, it is possible to prepare substituted nitroguanidines useful as an agricultural chemical (particularly, insecticide) or an intermediate therefor without using hydrolysis reaction. The process is excellent because it does not need a cumbersome operation which is otherwise required when an acid or water exists and it can prepare the target products in a high yield by a simple means.

EXAMPLES

The present invention will hereinafter be described more specifically by the following examples and comparative examples. The term "pretreatment" as will be used later in Examples 11 to Example 15 means washing a commercially-available agent with a reaction solvent subsequent to washing with methanol.

Incidentally, an analysis by high performance liquid chromatography (which will hereinafter be abbreviated as "HPLC") is made under the following conditions:

Column: L-column (Chemicals Inspection & Testing Institute, Japan)

Eluent: methanol/water or acetonitrile/water

Temperature: 40° C.

Flow rate: 1 ml/min.

Detector: UV 210, 254 or 278 nm

Example 1

To 5 g of 1-(2-chloro-5-pyridyl)methyl-3,5-dimethyl-2-nitroiminohexahydrotriazine, 20 g of methanol and 4.90 g of n-butylamine were added, followed by reflux for 6 hours. The reaction mixture was analyzed by HPLC. As a result, it was found to contain 3.96 g of 1-(2-chloro-5-pyridyl) methyl-3-methyl-2-nitroguanidine. Yield: 97.1%.
The reaction mixture was concentrated to half of its original volume and cooled to precipitate crystals. The crystals were isolated by filtration and were confirmed to have a target structure. Its physical properties are shown in Table 1.

Example 2

To 5 g of 1-(2-chloro-5-thiazolyl)methyl-3-methyl-5-benzyl-2-nitroiminohexahydrotriazine, 25 g of ethanol and 3.73 g of pyrrolidine were added, followed by stirring at 60° C. for 8 hours. The reaction mixture was analyzed by HPLC. As a result, it was found to contain 3.21 g of 1-(2-chloro-5-thiazolyl)methyl-3-methyl-2-nitroguanidine. Yield: 97.9%. The reaction mixture was concentrated, followed by the addition of water and ethyl acetate to cause separation. The organic layer was isolated by vacuum drying. It was found to have the target structure. Its physical properties are shown in Table 1.

Example 3

To 5 g of 1-(3-tetrahydrofuryl)methyl-3-methyl-5-isopropyl-2-nitroiminohexahydrotriazine, 25 g of isobutanol and 4.58 g of morpholine were added, followed by stirring at 100° C. for 4 hours. As a result of analysis of the reaction mixture by HPLC, it was found to contain 3.33 g of 1-(3-tetrahydrofuryl)methyl-3-methyl-2-nitroguanidine. Yield: 94.0%. The reaction mixture was cooled and crystals so precipitated were collected by filtration. They were then confirmed to have the target structure. Their physical properties are shown in Table 1.

Example 4

To 5 g of 1-(2-methyl-4-tetrahydrofuryl)methyl-3-methyl-5-ethyl-2-nitroiminohexahydrotriazine, 30 g of isopropanol and 1.58 g of ethylenediamine were added, followed by stirring at 70° C. The reaction mixture was analyzed by HPLC. As a result, it was found to contain 3.76 g of 1-(2-methyl-4-tetrahydrofuryl)methyl-3-methyl-2-nitroguanidine. Yield: 93.2%. The reaction mixture was concentrated, followed by purification by a silica gel column (ethyl acetate/acetone), whereby it was confirmed to have the target structure. Its physical properties are shown in Table 1.

Example 5

To 5 g of 1-(2-tetrahydrofuryl)methyl-3-allyl-5-t-butyl-2-nitroiminohexahydrotriazine, 20 g of ethylene glycol and 1.54 g of hydrazine monohydrate were added, followed by stirring at 50° C. for 12 hours. The reaction mixture was analyzed by HPLC. As a result, it was found to contain 3.33 g of 1-(2-tetrahydrofuryl)methyl-3-allyl-2-nitroguanidine. Yield: 94.9%. Its physical properties are shown in Table 1.

Example 6

In an autoclave, 5 g of 1-(3-tetrahydrofuryl)methyl-3-methyl-5-cyclohexyl-2-nitroiminohexahydrotriazine, 25 g of methanol and 4.77 g of a 40% methylamine/methanol solution were charged and they were reacted at 60° C. for 6 hours. The reaction mixture was analyzed by HPLC. As a result, it was found to contain 2.98 g of 1-(3-tetrahydrofuryl)methyl-3-methyl-2-nitroguanidine. Yield: 95.9%. Its physical properties are shown in Table 1.

Example 7

To 5 g of 1-(3-tetrahydrofuryl)methyl-3-methyl-5-ethyl-2-nitroiminohexahydrotriazine, 15 g of methanol, 5 g of water and 2.06 g of piperazine were added, followed by stirring at 60° C. for 5 hours. The reaction mixture was analyzed by HPLC. As a result, it was found to contain 3.44 g of 1-(2-tetrahydrofuryl)methyl-3-methyl-2-nitroguanidine. Yield: 92.3%. Its physical properties are shown in Table 1.

Example 8

To 15 g of 1-(2-chloro-5-pyridyl)methyl-3,5-dimethyl-2-nitroiminohexahydrotriazine, 150 g of dichloromethane and 13.1 g of morpholine were added, followed by pressurization to 1.0 MPa with nitrogen in an autoclave. When the contents were reacted at 90° C. for 4 hours, the reaction pressure was about 1.4 MPa. The reaction mixture was analyzed by HPLC. As a result, it was found to contain 12.05 g of 1-(2-chloro-5-pyridyl)methyl-3-methyl-2-nitroguanidine. Yield: 98.5%. The reaction mixture was concentrated to half of its original volume and then cooled to precipitate crystals. The crystals were isolated by filtration and they were confirmed to have the target structure. Their physical properties are shown in Table 1.

Example 9

To 15 g of 1-(2-chloro-5-thiazolyl)methyl-3-methyl-5-benzyl-2-nitroiminohexahydrotriazine, 150 g of dichloromethane and 6.01 g of ethanolamine were added, followed by pressurization to 1.0 MPa with nitrogen in an autoclave. When they were reacted at 80° C. for 8 hours, the reaction pressure was about 1.2 MPa. The reaction mixture was then analyzed by HPLC. As a result, it was found to contain 11.31 g of 1-(2-chloro-5-thiazolyl)methyl-3-methyl-2-nitroguanidine. Yield: 92.0%. About 50 g of saturated saline were added to the reaction mixture to cause separation. The organic layer was isolated by vacuum drying and was confirmed to have the target structure. Its physical properties are shown in Table 1.

Example 10

In 15 g of 1-(3-tetrahydrofuryl)methyl-3-methyl-5-isopropyl-2-nitroiminohexahydrotriazine, 150 g of dichloromethane were charged. In an autoclave, the resulting mixture was allowed to absorb about 1 g of an ammonia gas. The reaction was effected at 90° C. for 4 hours, after pressurizing to 1.0 MPa with nitrogen. Then, the pressure increased to about 1.3 MPa. The reaction mixture was analyzed by HPLC. As a result, it was found to contain 10.00 g of 1-(3-tetrahydrofuryl)methyl-3-methyl-2-nitroguanidine. Yield: 94.1%. The reaction mixture was added with about 30 g of an aqueous solution of a sodium sulfate, which had been made acidic with sulfuric acid, to cause separation, followed by extraction from the aqueous layer by using dichloromethane. The organic layer was concentrated under reduced pressure, followed by the addition of ethyl acetate to cause precipitation. The crystals so obtained were collected by filtration and they were confirmed to have the target structure. Isolation yield: 83%. Their physical properties are shown in Table 1.

Example 11

To 5 g of 1-(2-chloro-5-pyridyl)methyl-3,5-dimethyl-2-nitroiminohexahydrotriazine, 20 g of methanol and 12 g of "Lewatit OC1059" (trade name; product of Bayer AG) which had been pretreated were added, followed by reflux for 6 hours. The reaction material was collected by filtration and washed with methanol. The filtrate and wash liquid were combined and analyzed by HPLC. As a result, it was found to contain 3.79 g of 1-(2-chloro-5-pyridyl)methyl-3-methyl-2-nitroguanidine. Yield: 92.9%. The reaction mixture was concentrated to half of its original volume and then cooled to precipitate crystals. The crystals were isolated by filtration and they were confirmed to have the target structure. Their physical properties are shown in Table 1.

Example 12

To 5 g of 1-(2-chloro-5-thiazolyl)methyl-3-methyl-5-benzyl-2-nitroiminohexahydrotriazine, 25 g of ethanol and 11 g of "Diaion WA20" (trade name; product of Mitsubishi Chemical Co., Ltd.) which had been pretreated were added, followed by stirring at 60° C. for 8 hours. The reaction material was filtered, followed by washing with ethanol. The filtrate and wash liquid were combined and analyzed by HPLC. As a result, it was found to contain 2.95 g of 1-(2-chloro-5-thiazolyl)methyl-3-methyl-2-nitroguanidine. Yield: 90.0%. The reaction mixture was concentrated. Water and ethyl acetate were added to the concentrate to cause separation. The organic layer so obtained was isolated by vacuum drying and was confirmed to have the target structure. Its physical properties are shown in Table 1.

Example 13

To 5 g of 1-(3-tetrahydrofuryl)methyl-3-methyl-5-isopropyl-2-nitroiminohexahydrotriazine, 25 g of isobutanol and 15 g of "Lewatit OC1065" (trade name; product of Bayer AG) which had been pretreated were added, followed by stirring at 70° C. for 4 hours. The reaction material was filtered, followed by washing with isobutanol. The filtrate and wash liquid were combined and analyzed by HPLC. As a result, it was found to contain 3.37 g of 1-(3-tetrahydrofuryl)methyl-3-methyl-2-nitroguanidine. Yield: 95.1%. The reaction mixture was then cooled. The crystals so precipitated were collected by filtration and they were confirmed to have the target structure. Their physical properties are shown in Table 1.

Example 14

In 30 g of isopropanol, 5 g of 1-(2-methyl-4-tetrahydrofuryl)methyl-3-methyl-5-ethyl-2-nitroiminohexahydrotriazine were dissolved under heat. The resulting solution was allowed to pass through a column filled with 20 g of "Diaion WA21" (trade name; product of Mitsubishi Chemical Co., Ltd.), which had been subjected to pretreatment, at 70° C. The reaction material and the washing of the column were combined, followed by an analysis by HPLC. As a result, it was found to contain 3.72 g of 1-(2-methyl-4-tetrahydrofuryl)methyl-3-methyl-2-nitroguanidine. Yield: 92.2%. The reaction mixture was concentrated. The concentrate was then purified by a silica gel column (ethyl acetate/acetone) and was confirmed to have the target structure. Its physical properties are shown in Table 1.

Example 15

In a test tube filled with 40 g of "Cepabeades FP-BA13" (trade name; product of Mitsubishi Chemical Co., Ltd.) which had been pre-treated, a solution of 5 g of 1-(2-tetrahydrofuryl)methyl-3-allyl-5-t-butyl-2-nitroiminohexahydrotriazine in 20 g of ethylene glycol was charged, followed by agitation at 50° C. for 12 hours. The reaction material was filtered, followed by washing with methanol. The filtrate and wash liquid were combined and analyzed by HPLC. As a result, it was found to contain 3.09 g of 1-(2-tetrahydrofuryl)methyl-3-allyl-2-nitroguanidine. Yield: 88.1%. Its physical properties are shown in Table 1.

Example 16

To 5 g of 1-(3-tetrahydrofuryl)methyl-3-methyl-5-cyclohexyl-2-nitroiminohexahydrotriazine, 25 g of methanol and 14 g of "Lewatit R258-K" (trade name; product of Bayer AG) which was in the commercially-available form were added. The resulting mixture was reacted at 60° C. for 5 hours. The reaction material was filtered, followed by with methanol. The filtrate and wash liquid were combined and analyzed by HPLC. As a result, it was found to contain 2.84 g of 1-(3-tetrahydrofuryl)methyl-3-methyl-2-nitroguanidine. Yield: 91.4%. Its physical properties are shown in Table 1.

Example 17

To 5 g of 1-(3-tetrahydrofuryl)methyl-3-methyl-5-ethyl-2-nitroiminohexahydrotriazine, 25 g of methanol and 14 g of "Aminopropyl-CPG" (trade name; product of CPG Inc.) which was still in the commercially-available form were added. The resulting mixture was reacted at 80° C. for 4 hours. The reaction material was filtered, followed by wash liquid with methanol. The filtrate and washing were combined and analyzed by HPLC. As a result, it was found to contain 3.50 g of 1-(3-tetrahydrofuryl)methyl-3-methyl-2-nitroguanidine. Yield: 93.9%. Its physical properties are shown in Table 1.

Example 18

To 5 g of 1-(2-chloro-5-pyridyl)methyl-3,5-dimethyl-2-nitroiminohexahydrotriazine, 20 g of isobutanol and 2.21 g of ammonium sulfate were added, followed by stirring at 100° C. for 4 hours. The reaction mixture was filtered and the filtrate was analyzed by HPLC. As a result, it was found to contain 3.90 of 1-(2-chloro-5-pyridyl)methyl-3-methyl-2-niroguanidine. Yield: 95.6%. The reaction mixture was concentrated to half of its original volume and cooled to precipitate crystals. The crystals were isolated by filtration and were confirmed to have the target structure. Their physical properties are shown in Table 1.

Example 19

To 5 g of 1-(2-chloro-5-thiazolyl)methyl-3-methyl-5-benzyl-2-nitroiminohexahydrotriazine, 25 g of ethanol and 1.52 g of ammonium acetate were added, followed by reflux for 4 hours. The reaction mixture was analyzed by HPLC. As a result, it was found to contain 3.97 g of 1-(2-chloro-5-thiazolyl)methyl-3-methyl-2-nitroguanidine. Yield: 96.9%. The reaction mixture was concentrated. Water and ethyl acetate were added to the concentrate to cause separation. The organic layer so obtained was isolated by vacuum drying and it was confirmed to have the target structure. Its physical properties are shown in Table 1.

Example 20

To 5 g of 1-(3-tetrahydrofuryl)methyl-3-methyl-5-isopropyl-2-nitroiminohexahydrotriazine, 25 g of methanol and 0.94 g of ammonium chloride were added, followed by reflux for 4 hours. The reaction mixture was filtered and the filtrate was analyzed by HPLC. As a result, it was found to contain 3.47 g of 1-(3-tetrahydrofuryl)methyl-3-methyl-2-nitroguanidine. Yield: 97.9%. The reaction mixture was cooled and the crystals so precipitated were collected by filtration. The resulting crystals were confirmed to have the target structure. Their physical properties are shown in Table 1.

Example 21

To 5 g of 1-(2-methyl-4-tetrahydrofuryl)methyl-3-methyl-5-ethyl-2-nitroiminohexahydrotriazine, 30 g of n-butanol and 2.32 g of ammonium sulfate were added, followed by stirring at 110° C. for 5 hours. The reaction mixture was analyzed by HPLC. As a result, it was found to contain 3.69 g of 1-(2-methyl-4-tetrahydrofuryl)methyl-3-methyl-2-nitroguanidine. Yield: 97.4%. The reaction mixture was concentrated, purified by a silica gel column (ethyl acetate/acetone) and then confirmed to have the target structure. Its physical properties are shown in Table 1.

Example 22

To 5 g of 1-(2-tetrahydrofuryl)methyl-3-allyl-5-t-butyl-2-nitroiminohexahydrotriazine, 20 g of ethanol and 2.14 g of ammonium phosphate were added, followed by reflux for 5 hours. The reaction mixture was analyzed by HPLC. As a result, it was found to contain 3.30 g of 1-(2-tetrahydrofuryl)methyl-3-allyl-2-nitroguanidine. Yield: 95.9%. Its physical properties are shown in Table 1.

Example 23

In an autoclave, 5 g of 1-(3-tetrahydrofuryl)methyl-3-methyl-5-cyclohexyl-2-nitroiminohexahydrotriazine, 25 g of methanol and 1.48 g of ammonium carbonate were charged, followed by reaction at 100° C. for 10 hours. The reaction pressure was 0.2 Mpa. As a result of an analysis of the reaction mixture by HPLC, it was found to contain 2.99 g of 1-(3-tetrahydrofuryl)methyl-3-methyl-2-nitroguanidine. Yield: 96.2%. Its physical properties are shown in Table 1.

Example 24

To 5 g of 1-(3-tetrahydrofuryl)methyl-3-methyl-5-ethyl-2-nitroiminohexahydrotriazine, 20 g of methanol and 2.77 g of diammonium monohydrogenphosphate were added, followed by stirring at 60° C. for 5 hours. As a result of an analysis of the reaction mixture by HPLC, it was found to contain 3.53 g of 1-(2-tetrahydrofuryl)methyl-3-methyl-2-nitroguanidine. Yield: 94.7%. Its physical properties are shown in Table 1.

Example 25

To 5 g of 1-(2-choro-5-pyridyl)methyl-3,5-dimethyl-2-nitroiminohexahydrotriazine, 20 g of isobutanol and 2.26 g of methylamine hydrochloride were added, followed by stirring at 100° C. for 4 hours. The insoluble matter was filtered off. The filtrate and wash liquid were combined and analyzed by HPLC. As a result, it was found to contain 3.81 g of 1-(2-chloro-5-pyridyl)methyl-3-methyl-2-nitroguanidine. Yield: 93.4%. The filtrate and combined wash liquid was concentrated to half of its original volume and cooled to precipitate crystals. The crystals were isolated by filtration and they were confirmed to have the target structure. Their physical properties are shown in Table 1.

Example 26

To 5 g of 1-(2-chloro-5-thiazolyl)methyl-3-methyl-5-benzyl-2-nitroiminohexahydrotriazine, 25 g of n-butanol and 2.23 g of morpholine sulfate were added, followed by reflux for 4 hours. The insoluble matter was filtered off and the filtrate and wash liquid were combined and analyzed by HPLC. As a result, it was found to contain 3.73 g of 1-(2-chloro-5-thiazolyl)methyl-3-methyl-2-nitroguanidine. Yield: 91.1%. The filtrate and combined wash liquid was concentrated, followed by the addition of water and ethyl acetate to cause separation. The organic layer so obtained was isolated by vacuum drying and confirmed to have the target structure. Its physical properties are shown in Table 1.

Example 27

To 5 g of 1-(3-tetrahydrofuryl)methyl-3-methyl-5-isopropyl-2-nitroiminohexahydrotriazine, 25 g of isobutanol and 1.40 g of methylamine sulfate were added, followed by reflux for 4 hours. The insoluble matter was filtered off. The filtrate and wash liquid were combined and analyzed by HPLC. As a result, it was found to contain 3.33 g of 1-(3-tetrahydrofuryl)methyl-3-methyl-2-nitroguanidine. Yield: 94.0%. The filtrate and combined wash liquid was cooled and crystals so precipitated were collected by filtration. The crystals were confirmed to have the target structure. Their physical properties are shown in Table 1.

Example 28

To 5 g of 1-(2-methyl-4-tetrahydrofuryl)methyl-3-methyl-5-ethyl-2-nitroiminohexahydrotriazine, 30 g of n-butanol and 4.98 g of pyrrolidine hydrochloride were added, followed by stirring at 110° C. for 5 hours. The insoluble matter was filtered off. As a result of an analysis of the filtrate and combined wash liquid by HPLC, it was found to contain 3.47 g of 1-(2-methyl-4-tetrahydrofuryl) methyl-3-methyl-2-nitroguanidine. Yield: 91.6%. The filtrate and combined wash liquid was concentrated and purified by a silica gel column (ethyl acetate/acetone). It was confirmed to have the target structure. Its physical properties are shown in Table 1.

Comparative Example 1

To 8.5 g of 1-(2-chloro-5-pyridyl)methyl-3,5-dimethyl-2-nitroiminohexahydrotriazine, 90 ml of ethanol and 5.5 ml of 6M hydrochloric acid were added, followed by heating under reflux for 30 minutes. Since hydrochloric acid made the reaction mixture acidic, cooling of the reaction mixture did not cause precipitation of crystals.

Comparative Example 2

To 18 g of 1-(3-tetrahydrofuryl)methyl-3,5-dimethyl-2-nitroiminohexahydrotriazine, 340 g of dichloromethane were charged. To the resulting mixture, 155 g of 7% hydrochloric acid were added, followed by heating under reflux for 4 hours. The reaction mixture was cooled and then added with 33 g of sodium chloride to cause separation. The water layer so obtained was extracted four times with 50 g of dichloromethane. The extraction ratio was 83%5. The organic layers were combined, followed by concentration under reduced pressure. To the concentrate, ethyl acetate was added to cause precipitation, whereby 9.24 g of 1-(3-tetrahydrofuryl)methyl-3-methyl-2-nitroguanidine were obtained. Isolation yield: 66.4%.

Comparative Example 3

To 20 g of 1-(3-tetrahydrofuryl)methyl-3-methyl-5-isopropyl-2-nitroiminohexahydrotriazine, 140 g of dichloromethane were charged, To the resulting mixture, 106 g of 13% sulfuric acid were added, followed by heating under reflux for 8 hours. The reaction yield was 98%. It was cooled and then adjusted to pH 6.5 with a 45% sodium hydroxide solution. As a result, 1-(3-tetrahydrofuryl)methyl-3-methyl-5-isopropyl-2-nitroiminohexahydrotriazine showed an increase by 9%. The reaction mixture was then separated. The water layer so obtained was re-extracted with 140 g of dichloromethane. The organic layers were combined and concentrated under reduced pressure. Ethyl acetate was added to the concentrate to cause precipitation, whereby 10.3 g of 1-(3-tetrahydrofuryl)methyl-3-methyl-2-nitroguanidine were obtained. Isolation yield: 73%.

TABLE 1

| A | $R_2$ | Physical properties |
|---|---|---|
| 2-Chloro-5-pyridyl | Methyl | $\delta_{TMS}$ (DMSO-$d_6$)ppm: 2.83 (3H, br-s), 4.42 (2H, br-s), 7.48 (1H, d, J=8.1Hz), 7.78 (1H, dd, J=8.1Hz, J=2.2Hz), 7.92 (1H, br), 8.35 (1H, d, J=2.2Hz), 9.14(1H, br). $\nu_{max}$ (KBr) cm$^{-1}$: 3274, 1620, 1573, 1236. m.p. 156.3 to 157.0° C. Elemental analysis found: C 39.74, H 4.10, N 27.89, Cl 14.09 cal: C 39.44, H 4.14, N 28.74, Cl 14.55 |
| 2-Chloro-5-thiazolyl | Methyl | $\delta_{TMS}$ (DMSO-$d_6$) ppm: 2.80 (3H, s), 4.49 (2H, br-s), 7.58 (1H, s), 7.93 (1H, br), 9.13 (1H, br). $\nu_{max}$ (KBr) cm$^{-1}$: 3332, 1630, 1542, 1261. m.p. 172.1 to 172.8° C. (decomposed) Elemental analysis found: C 28.77, H 3.00, N 27.73, S 12.72, Cl 14.14 cal: C 28.86, H 3.23, N 28.05; S 12.84, Cl 14.20 |
| 3-Tetrahydrofuryl | Methyl | $\delta_{TMS}$ (CDCl$_3$) ppm: 1.62–1.74 (1H, m), 2.09–2.22 (1H, m), 2.59–2.79 (1H, m), 2.96 (3H, d, J=5.1Hz), 3.35 (2H, t, J=5.1Hz), 3.66–3.80 (3H, m), 3.92–4.08 (1H, m). |

TABLE 1-continued

| A | $R_2$ | Physical properties |
|---|---|---|
| 2-Methyl-4-tetrahydrofuryl | Methyl | $\nu_{max}$ (KBr) cm$^{-1}$: 3339, 3280, 1618, 1231.<br>m.p. 99.5 to 100.7° C.<br>$\delta_{TMS}$ (CDCl$_3$) ppm: 1.23 (3H*⅔, d, J=6.6Hz), 1.31 (3H*⅓, d, J=5.9Hz), 1.81–1.90 (1H*⅔, m), 2.24–2.34 (1H*⅓, m), 2.57–2.71 (1H, m), 2.96 (3H, d, J=5.1Hz), 3.32–3.35 (2H, m), 3.52–3.57 (1H, m), 3.75–3.77 (1H, m), 3.96–4.02 (1H, m), 4.11–4.19 (1H, m). |
| 2-Tetrahydrofuryl | Allyl | $\nu_{max}$ (neat) cm$^{-1}$: 3305, 1618, 1561, 1236.<br>$\delta_{TMS}$ (CDCl$_3$) ppm: 1.54–1.73 (1H, m), 1.87–2.20 (3H, m), 3.18–3.35 (1H, m), 3.54–3.71 (1H, m), 3.75–3.95 (2H, m), 4.01–4.15 (3H, m), 5.32–5.39 (2H, m), 5.82–5.96 (1H, m), 6.93 (1H, br), 9.41 (1H, br).<br>$\nu_{max}$ (KBr) cm$^{-1}$: 3293, 1612, 1213. |

What is claimed is:

1. A process for the preparation of a nitroguanidine derivative represented by the following formula (2):

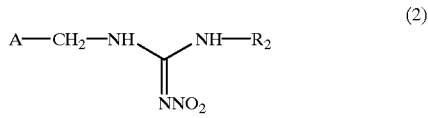

(2)

wherein A represents a substituted or unsubstituted aromatic or non-aromatic hydrocarbon ring, a substituted or unsubstituted aromatic or non-aromatic heterocycle, a hydrogen atom or a substituted or unsubstituted alkyl, alkenyl or alkynyl group and $R_2$ represents a hydrogen atom or a substituted or unsubstituted $C_{1-6}$ alkyl, alkenyl or alkynyl group, which comprises reacting a compound represented by the following formula (1):

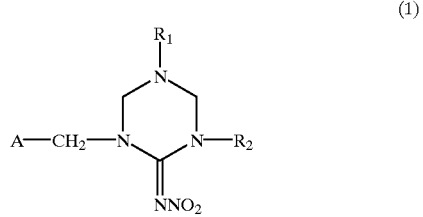

(1)

wherein $R_1$ represents a substituted or unsubstituted, linear or cyclic $C_{1-10}$ alkyl group and A and $R_2$ have the same meanings as defined above, with ammonia, primary amine or secondary amine or salt thereof.

2. A process according to claim 1, wherein said reaction is effected in a non-aqueous system.

3. A process according to claim 1, wherein said compound of the formula (1) is reacted with ammonia.

4. A process according to claim 1, wherein said compound of the formula (1) is reacted with an aliphatic amine.

5. A process according to claim 1, wherein said compound of the formula (1) is reacted with an ammonium salt or amine salt.

6. A process according to claim 1, wherein in said formulas (1) and (2), A represents a substituted or unsubstituted pyridyl, thiazolyl, oxazolyl or tetrahydrofuryl group.

7. A process according to claim 1, wherein in said formulas (1) and (2), A represents a 2-chloro-5-pyridyl, 2-chloro-5-thiazolyl, 2-tetrahydrofuryl or 3-tetrahydrofuryl group.

* * * * *

UNITED STATES PATENT AND TRADEMARK OFFICE
CERTIFICATE OF CORRECTION

PATENT NO. : 6,118,007
DATED : September 12, 2000
INVENTOR(S) : Koichi Ebihara et al.

It is certified that error appears in the above-identified patent and that said Letters Patent is hereby corrected as shown below:

Title page,
Item [75], please change the residence of inventor Tatsuo Kaiho to -- Chiba, Japan --.

Signed and Sealed this

Eighteenth Day of December, 2001

Attest:

Attesting Officer

JAMES E. ROGAN
Director of the United States Patent and Trademark Office